(12) United States Patent
Schrattenholz

(10) Patent No.: US 7,824,923 B2
(45) Date of Patent: Nov. 2, 2010

(54) NEUREGULIN-β ISOFORMS ASSOCIATED WITH NEURONAL PROCESSES

(75) Inventor: André Schrattenholz, Mainz (DE)

(73) Assignee: ProteoSys Ag, Mainz (DE)

( * ) Notice: Subject to any disclaimer, the term of this patent is extended or adjusted under 35 U.S.C. 154(b) by 132 days.

(21) Appl. No.: 10/485,870

(22) PCT Filed: Aug. 6, 2002

(86) PCT No.: PCT/EP02/08778

§ 371 (c)(1),
(2), (4) Date: Feb. 5, 2004

(87) PCT Pub. No.: WO03/014156

PCT Pub. Date: Feb. 20, 2003

(65) Prior Publication Data

US 2004/0197822 A1 Oct. 7, 2004

Related U.S. Application Data

(60) Provisional application No. 60/309,773, filed on Aug. 6, 2001, provisional application No. 60/341,809, filed on Dec. 21, 2001.

(51) Int. Cl.
A61K 49/00 (2006.01)
G01N 33/567 (2006.01)
G01N 33/558 (2006.01)
G01N 33/561 (2006.01)
G01N 33/53 (2006.01)

(52) U.S. Cl. ............... 436/516; 436/514; 436/173; 435/7.1; 424/9.2

(58) Field of Classification Search ............... None
See application file for complete search history.

(56) References Cited

U.S. PATENT DOCUMENTS 5,530,109 A * 6/1996 Goodearl et al. ............ 536/23.5

FOREIGN PATENT DOCUMENTS

| WO | WO 92/20798 A1 | 11/1992 |
|---|---|---|
| WO | WO 96/15812 A1 | 5/1996 |
| WO | WO 96/30403 A1 | 10/1996 |
| WO | WO 99/18976 A1 | 4/1999 |
| WO | WO 01 26607 A | 4/2001 |
| WO | WO 01 58948 A | 8/2001 |

OTHER PUBLICATIONS

Falls. Exp. Cell Res. 2003. 284: 14-30.*
Eilam et al. Proc. Natl. Acad. Sci. USA. 1998. 95: 1888-1893.*
Brown et al. J. Psychia Res. 1997. 31: 605-619.*
Nybo et al. Scand J. Immunol. 1998. 48: 350-356.*
Eilam R. et al., "Activity-dependent regulation of Neu Differentiation Factor/Neuregulin expression in rat brain", Proceedings of the National Academy of Sciences of USA, vol. 95, Feb. 1998, pp. 1888-1893.
Wen D. et al., "Structural and Functional Aspects of the Multiplicity of Neu Differentiation Factors", Molecular and Cellular Biology, vol. 14, No. 3, Mar. 1, 1994, pp. 1909-1919.
Chen J. et al., "Neuregulin signalling is mediated by erbB4 and activates CREB in hippocampal neurons", Society for Neuroscience Abstracts, vol. 26, No. 1-2, 2000.
Ozaki M., et al., "Neuregulin-beta induces expression of an NMDA-receptor subunit", Letters to Nature, vol. 390, 1997, pp. 691-694.
Marchionni et al., "Neuregulins as Potential Drugs for Neurological Disorders," Cold Spring Harbor Symposia on Quantitative Biology, vol. LXI, Cold Spring Harbor Laboratory Press, 61:459-472, 1996.
Sheldon, A. L. & M. B. Robinson: "The role of glutamate transporters in neurodegenerative diseases and potential opportunities for intervention", Neurochem Int. Nov.-Dec. 2007, 51 (6-7), pp. 333-355 [Epub Apr. 19, 2007].
Caudle, W. M.: "Glutamate, excitotoxicity, and programmed cell death in Parkinson disease.", Exp Neurol., Dec. 2009, 220(2), pp. 230-3 [Epub Oct. 6, 2009].
Graus et a).: "Antibodies and neuronal autoimmune disorders of the CNS", J. Neurol., Dec. 25, 2009 [Epub ahead of print].
Wikipedia article "AP-5", Dec. 18, 2009.
Morris, R. G.: "Synaptic Plasticity and Learning: Selective Impairment of Learning in Rats and Blockade of Long-Term Potention in vivo by the N-Methyl-D-Aspartate Receptor Antagonist AP5", Journal of Neuroscience, Sep. 1989, 9(9): 3040-57.
Wikipedia article CNQX, May 20, 2009.
Jane et al.: "Stereospecific antagonism by (+)-a-methyl-4-carboxyphenylglycine (MCPG) of 1S13R-ACPD induced effects in neonatal rat motoneurones and rat thalamic neurones", Neuropharmacology 32:725, 1993.
Sekiyama et al.: "Structure-activity relationships of new agonists and antagonists of different metabotropic glutamate receptor subtypes", Br. J. Pharmacol.I 17:1493, 1996.

(Continued)

Primary Examiner—Christine J Saoud
Assistant Examiner—Chang-Yu Wang
(74) Attorney, Agent, or Firm—Rothwell, Figg, Ernst & Manbeck, P.C.

(57) ABSTRACT

The invention relates to novel neuregulin-β isoforms associated with neuronal processes.

2 Claims, 7 Drawing Sheets

OTHER PUBLICATIONS

Bordi et al.: "Effects of the metabotropic glutamate receptor antagonist MCPG on spatial and context-specific learning", Neuropharmacology 35: 1557, 1996.

Wikipedia article "Nifedipine", Jan. 10, 2010.

Imamachi, N. et al.: "The Non-NMDA Glutamate Receptor Antagonist CNQX Augments Lidocaine Antinociception Through a Spinal Action in Rats", Anesth Analg 1999; 89:416-21.

Buonanno et al. ("Neuregulin and ErbB receptor signaling pathways in the nervous system", Curr. Opin. Neurobiol., 2001, vol. 11, No. 3, pp. 287-296).

Watkins et al., "Phenylglycine derivatives as antagonists of metabotropic glutamate receptors", TiPS Sep. 1994, (vol. 15), pp. 333-342.

* cited by examiner

Fig. 4: Average SV in the three collectives of rats

Fig. 5: Neu-ß SV relations before learning performance

Fig. 6: Neu-ß SV relations after learning performance

NEUREGULIN-β ISOFORMS ASSOCIATED WITH NEURONAL PROCESSES

CROSS REFERENCE TO RELATED APPLICATION

This application is a 35 USC §371 National Phase Entry Application from PCT/EP02/08778, filed Aug. 6, 2002, and designating the U.S. which claims the benefit of provisional application Nos. 60/309,773 filed Aug. 6, 2001 and 60/341,809 filed Dec. 21, 2001.

The invention relates to novel neuregulin-β isoforms associated with neuronal processes and to the use of neuregulin-β isoforms as a target for modulating the memory performance and particularly for enhancing the learning capacity in a mammal.

Neuregulins (also ARIA, neurogenic differentiation factors, heregulins and DDF) belong to a family of wide-spread and known growth and differentiation factors. For example in publication Ozaka M. et al., Nature 1997, Dec. 10-25, 390 (6661): 691-4 the inducing influence of neuregulin-β on the expression of the NR2C subunit of the NMDA receptor is described.

WO99/18976 describes a method for the treatment and/or prophylaxis of neurological diseases comprising administering a neuregulin, or a fragment or derivative of a neuregulin, or a nucleic acid coding for a neuregulin or a neuregulin fragment or derivative thereof to a patient. In WO99/18976 only tests on gene level are performed. Since up to over 100 different molecular protein species can be generated from one single gene by modifications on transcript or/and protein level, the indications in WO99/18976 are not sufficient to identify the protein species actually relevant to neurological processes.

WO98/55611 describes the use of a 15 bp-long neuregulin-response-element in therapeutical processes and screening methods for the identification of active agents.

PCT/EP01/01424 discloses a neuregulin-β isoform having an isoelectric point of ≦pH 7, particularly from pH 4.3 to pH 5.0 and more particularly from pH 4.5 to pH 4.7. This neuregulin-β isoform was obtained from hippocampal primary cultures from pre- or neonatal rats and characterized as indicator or target, respectively, for neuronal processes. Further, neuregulin-β could be identified as target in case of Morbus Alzheimer.

Surprisingly, with the help of new techniques of proteome analysis further neuregulin-β isoforms could be identified associated with neuronal processes. These novel neuregulin-β isoforms derived from rats (*rattus norvegicus*) exhibit the following properties in view of the isoelectric point and the apparent molecular weight:

| Apparent isoelectric point | Apparent molecular weight [kD] |
|---|---|
| 4, 3 | 36 |
| 4, 6 | 34 |
| 4, 6 | 36 |
| 4, 9 | 52 |
| 4, 9 | 28 |
| 4, 9 | 29 |
| 5, 1 | 24 |
| 5, 1 | 29 |
| 5, 15 | 21 |
| 5, 15 | 24 |
| 5, 2 | 29 |
| 5, 9 | 18 |
| 8, 5 | 51 |

-continued

| Apparent isoelectric point | Apparent molecular weight [kD] |
|---|---|
| 8, 5 | 52 |
| 9, 0 | 52 |
| 5, 9 | 34 |
| 6, 0 | 36 |
| 7, 2 | 52 |
| 7, 5 | 52 |
| 7, 5 | 48 |
| 7, 6 | 52 |
| 7, 8 | 48 |
| 7, 8 | 24 |
| 7, 9 | 24 |
| 8, 0 | 48 |
| 8, 0 | 52 |
| 8, 4 | 52 |
| 9, 5 | 52 |

The values of Table 1 are obtained under the experimental conditions described in the examples. The values are to be interpreted that in view of the isoelectric point there is a deviation of ±0.1, preferably ±0.05 and more preferably ±0.01 and in view of the apparent molecular weight there is a deviation of ±2 kd, particularly preferred ±1 kd and mostly preferred 0.5 kd.

Apart from the isoforms as indicated above, the present application also comprises combinations of at least two of the isoforms mentioned as well as corresponding isoforms from other mammalian species, particularly human neuregulin-β isoforms. The neuregulin-β isoforms according to the invention can be obtained from neuronal mammalian cells, e.g. rat cells or human cells, by known methods, e.g. immune adsorption using anti-neuregulin-β antibodies, optionally in combination with a fractionation according to the isoelectric point and according to the size.

A further subject matter of the present application is a pharmaceutical composition comprising at least one neuregulin-β isoform as described above, optionally together with pharmaceutically acceptable carriers, diluents and/or adjuvants. The pharmaceutical compositions preferably include the active ingredients in an effective amount to achieve the intended, e.g. diagnostic or therapeutic purpose. In addition to the active ingredients, the pharmaceutical compositions may contain pharmaceutically acceptable carriers, diluents and/or adjuvants. Details on techniques for formulation and administration may be found in the latest edition of Remington's Pharmaceutical Sciences (Maack Publishing Co., Easton, Pa.). The neuregulin-β isoforms or pharmaceutical compositions containing said neuregulin-β isoforms may be used for the monitoring or modulation of neuronal processes. Furthermore, the isoforms and the pharmaceutical compositions may be used as a target in a method of identifying novel pharmaceutical agents, i.e. as a target in a screening method, particularly for identifying pharmaceutical agents suitable for monitoring or modulating neuronal processes.

More particularly, the neuregulin-β isoforms are suitable for the monitoring or modulation of neuronal diseases, particularly neuronal degenerative diseases such as Morbus Alzheimer. Furthermore, the neuregulin-β isoforms may be used as a target in a method for identifying novel pharmaceutical agents which are suitable for monitoring or modulating neuronal diseases, particularly neuronal degenerative diseases such as Morbus Alzheimer.

One embodiment of the invention relates to the use of the novel neuregulin-β isoforms as indicator in a method for monitoring neuronal processes. This embodiment preferably relates to a diagnostic method comprising the determination of the presence, the concentration and/or the activity of neuregulin-β isoforms or combinations of isoforms in a sample, e.g. a biological sample which may be obtained from body fluids or tissue, particularly neuronal fluids or tissue (in vitro diagnosis) or in an organism (in vivo diagnosis). This diagnostic method preferably comprises a detection on the protein level, e.g. by immunological methods. Such diagnostics methods are well known.

A further particular embodiment relates to the use of neuregulin-β isoforms as a target in a method for modulating neuronal processes. This embodiment may comprise an alteration, e.g. a decrease or increase of the concentration, localization and/or activity of neuregulin-β isoforms or combinations of isoforms, preferably in neuronal fluids or tissue such as in the brain, in the spinal cord and/or in neuronal cells.

Further, the invention relates to the use of an active agent influencing the expression and/or function of neuregulin-β, neuregulin-β variants and/or members of the neuregulin-β signal transduction pathway for the preparation of a therapeutic drug or a pharmaceutical composition for the treatment of disturbances or illnesses that are linked with neuregulin-β-related cellular malfunctions.

This method may comprise the administration of neuregulin-β inhibitors, e.g. antibodies or low molecular weight substances and/or the administration of neuregulin-β antisense nucleic acids, if a reduction of neuregulin-β concentration and/or activity is desired. On the other hand, the administration of neuregulin-β or of a nucleic acid coding therefor may take place at a target site in the organism, if an increase of the amount of neuregulin-β and/or its activity is desired. Neuregulin-β may be administered in free form or associated with a suitable carrier, e.g. vehicles such as micelles, liposomes etc. The administration of nucleic acids encoding neuregulin-β may be carried out in form of so-called "naked" DNA or in form of vehicles as indicated above, or, alternatively, in form of viral vectors, e.g. adenoviruses, retroviruses etc.

Alternatively or additionally, also substances may be administered, which influence the expression and/or the state of the neuregulin-β isoforms or combinations thereof. These substances, e.g. inhibitors or activators may be identified easily by using the effect space/effector space analysis process as described in PCT/EP01/01424 to the invention or by other screening methods. The invention therefore also comprises such substances, e.g. low molecular weight active agents and/or biological substances, e.g. macromolecules such as proteins, nucleic acids etc. and substances derived therefrom by modifications as well as their application in diagnostic and therapeutic processes.

Furthermore, the invention relates to the use of a substance detecting the above signal elements for the diagnosis of disturbances or illnesses linked with neuregulin-β-related cellular malfunctions.

In a preferred embodiment of diagnostic and therapeutic processes neuronal diseases are detected or influenced, respectively, in particular neuronal degenerative diseases such as Morbus Alzheimer.

A still further preferred embodiment of the present invention relates to a method of producing novel pharmaceutical agents comprising assaying the effect of a compound on at least one neuregulin-β isoform as described above, and identifying compounds which alter the amount, localization and/or characteristics of the at least one neuregulin-β isoform.

Preferably the effect of a compound on neuregulin-β isoforms is assayed by a multidimensional effect space/effector space method as described in PCT/EP01/01424. More preferably, neuronal cell cultures are provided, e.g. by plating on glass cover slips coated with poly-L-lysine at a density ranging from 75 000 to 1 500 000 $cm^{-2}$. Cells are loaded with a fluorescent dye, e.g. fura-2, a calcium sensitive fluorescent dye. Then the cells are stimulated, e.g. by applying a calcium containing buffer. The effect of a test compound on the system with or without stimulation may be determined by proteome analytic methods.

A compound which has been identified as an effector of neuregulin-β isoforms as described above may be used for the preparation of a pharmaceutical composition. Alternatively, the compound may be used as a drug lead structure in order to obtain further compounds which are derived therefrom, e.g. by empirical derivatization and/or computer modelling. A compound which has been identified by the method as described above or a compound derived therefrom may be formulated as a pharmaceutical composition, particularly for the diagnosis and/or therapy of neuronal diseases, more preferably neuronal degenerative diseases such as Morbus Alzheimer.

Furthermore, the present invention relates to a method of enhancing the memory performance, in particular the learning capacity, in an animal by modulating the neuregulin-βisoform pattern. This effect is described in Example 3, wherein a behaviour test with experimental animals has been carried out. The results demonstrate the existence of a tight correlation between the concentration of the memory-relevant neuregulin-β isoform in the rat's hippocampi and the learning capacity of the rat during the test training. A high concentration of the memory-relevant neuregulin-β isoform in neuronal cells, particularly in brain cells, corresponds to a good memory performance of an animal and an improvement in the learning capacity, whereas a low concentration of the neuregulin-β isoform in the rat's hippocampi indicates a low test performance. In particular, the method of enhancing the learning capacity comprises increasing the amount of a neuregulin-β isoform having an isoelectric point in the range of from pH 4.3 to 5.0 and an apparent molecular weight of about 32 kDa (SDS-PAGE). This neuregulin-β isoform is disclosed in PCT/EP01/01424 and derived from rats (*rattus norvegicus*). It should be particularly noted that the corresponding human neuregulin-β isoform is an especially preferred embodiment of the invention.

Thus, the invention also relates to a method of enhancing the memory performance in an animal, particularly in a mammal, more particularly in a human, wherein the neuregulin-β isoform pattern is modulated. This modulation preferably comprises an increase in the amount of a particular neuregulin-β isoform species, e.g. a rat neuregulin-β isoform or the corresponding human neuregulin-β isoform.

Further, the invention relates to the use of a modulator of the neuregulin-β isoform pattern in neuronal cells for the manufacture of an agent for enhancing the memory performance in an animal.

Further, the invention is elucidated in more detail by the following figures and examples:

EXAMPLE

1. Materials and Methods

1.1 Primary Cell Culture

Figure 1:
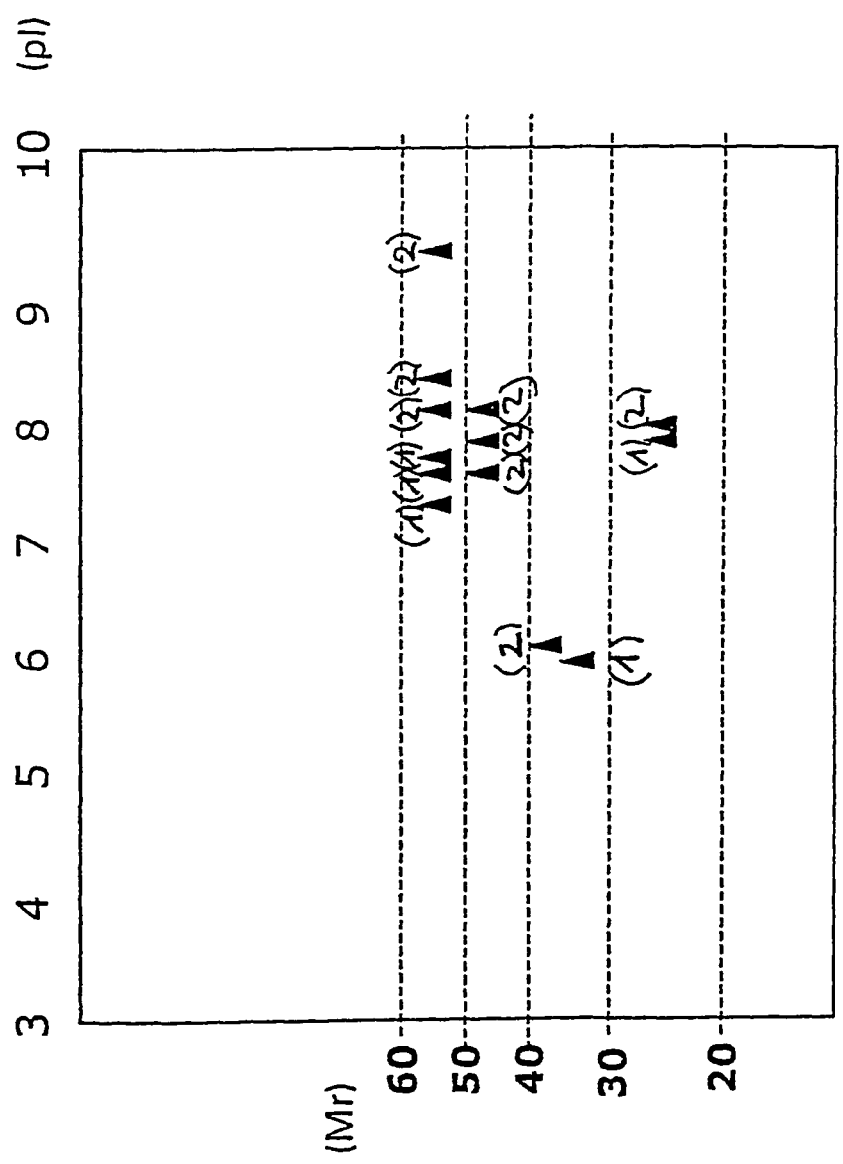
FIG. 1 shows the appearance of neuregulin-β isoforms from hippocampal tissue sections (rat).
(1): after prestimulation.
(2): control without prestimulation.

Cell cultures with prevailing CA1 neurons were prepared using hippocampi from female neonatal Sprague-Dawley rats as described (Brewer, J. Neurosci. Res (1995), 674-683). Neuronal cells were plated on glass coverslips coated with poly-L-lysine at a density ranging from 75,000 to 150,000 $cm^{-2}$.

1.2 Fura-2 $Ca^{2+}$-Imaging

Cells were loaded with the fluorescent dye fura-2 AM (2 mM, Molecular Probes, Leiden, The Netherlands) for 40 min, subsequent deesterification time was 30 min. For imaging an inverted light microscope (Axiovert 100, ZEISS, Germany), equipped with an UV-illumination source (75 W XBO lamp, OSRAM, Germany) was used at excitation wavelengths of 340 ($I_1$) and 380 ($I_2$) nm, and emission wavelength of 510 nm. Acquisition and analysis of the data were performed by using MetaFluor software (Universal Imaging Corporation). Image resolution was 168×129 pixels (binning 8×8, pixel size 6.8× 6.8 mm). Only cells which were by identified as neurons by immunostaining (not shown or FIG. 2x) and whose calcium levels returned to the resting state after first stimulation were taken into account. The system was calibrated using solutions containing $(Ca^{2+})_0$ and $(Ca^{2+})_{max}$ obtained from Molecular Probes, and an equation calibration method described elsewhere[6]: $[(Ca^{2+})_i = K_d(F_{min}/F_{max})(R-VR_{min})/(VR_{max}-R)]$ (Kd=224 nM, $F_{min}/F_{max}$ and $R_{min}/R_{max}$ represent $I_2$- and ratio-image intensities at zero and saturating ($Ca^{2+}$), respectively. V, a viscosity factor was taken to be 1).

1.3 Stimulation of Neurons

Every group of cells was stimulated twice for 30 s (one pair of images being acquired every five seconds), with 30 min between ligand applications. Stimulation buffer for the $Ca^{2+}$-imaging experiments contained, in mM: 125 NaCl, 5 KCl, 6 $CaCl_2$, 0.8 $MgCl_2$, 5 glucose, 20 HEPES; pH 7.3, and was added (in mM) 50 L-glutamate, 10 glycine (Sigma), 10 bicuculline, 25 APV, 10 CNQX, 500 (S)-MCPG and 10 nifedipine (Tocris), as explained elsewhere in the text. Washing buffer was (in mM): 125 NaCl, 5 KCl, 2 $KH_2PO_4$, 2 $CaCl_2$, 1 $MgCl_2$, 5 glucose, 20 HEPES; pH 7.3.

1.4 Immunochemistry

Primary hippocampal neurons have been labelled by means of indirect immunofluorescence. Primary antibody used in these experiments was directed against a-Tau protein as neuronal marker (IgG, rabbit, polyclonal), diluted 1:100. Secondary antibody (goat, IgG, anti-rabbit, Texas Red-coupled, Jackson Research) was diluted 1:200.

1.5 Proteomics

Immobilone DryStrips (pH 4-7, AmershamPharmacia Biotech) were reswollen overnight in 300 μL of protein solution (400 μg of hippocampal protein). Prior to electrophoresis using an IPGphor IEF unit (AmershamPharmacia Biotech), IEF gels were equilibrated with DDT- and iodoacetamide containing buffers, SDS-PAGE was performed in a Hofer Dalt unit (AmershamPharmacia Biotech). After visualization by silver staining and spot picking, gel pieces were destained with a solution of 25 mM ammonium bicarbonate/50% acetonitrile and proteins were digested as described elsewhere[7]. For MALDI-TOF mass spectrometry, samples were dissolved in 5 μL of 50% acetonitrile/0.1% trifluoroacetic acid and sonicated for a few minutes. Aliquots of 0.5 μL were applied onto a target disc and spectra were obtained using a Bruker Biflex MALDI time-of-flight mass spectrometer as described[7]. MS/MS analysis was carried out using a Finnegan Mat (San Jose, USA) LCQ ion trap mass spectrometer. For interpretation of the MS and MS/MS spectra of protein digests, we used the Sherpa software, the MS-Fit program, the Pro-Found program, the PepSearch program from EMBL in Heidelberg and TagIdent available on the ExPASy world wide web server.

2. Results

Figure 2:
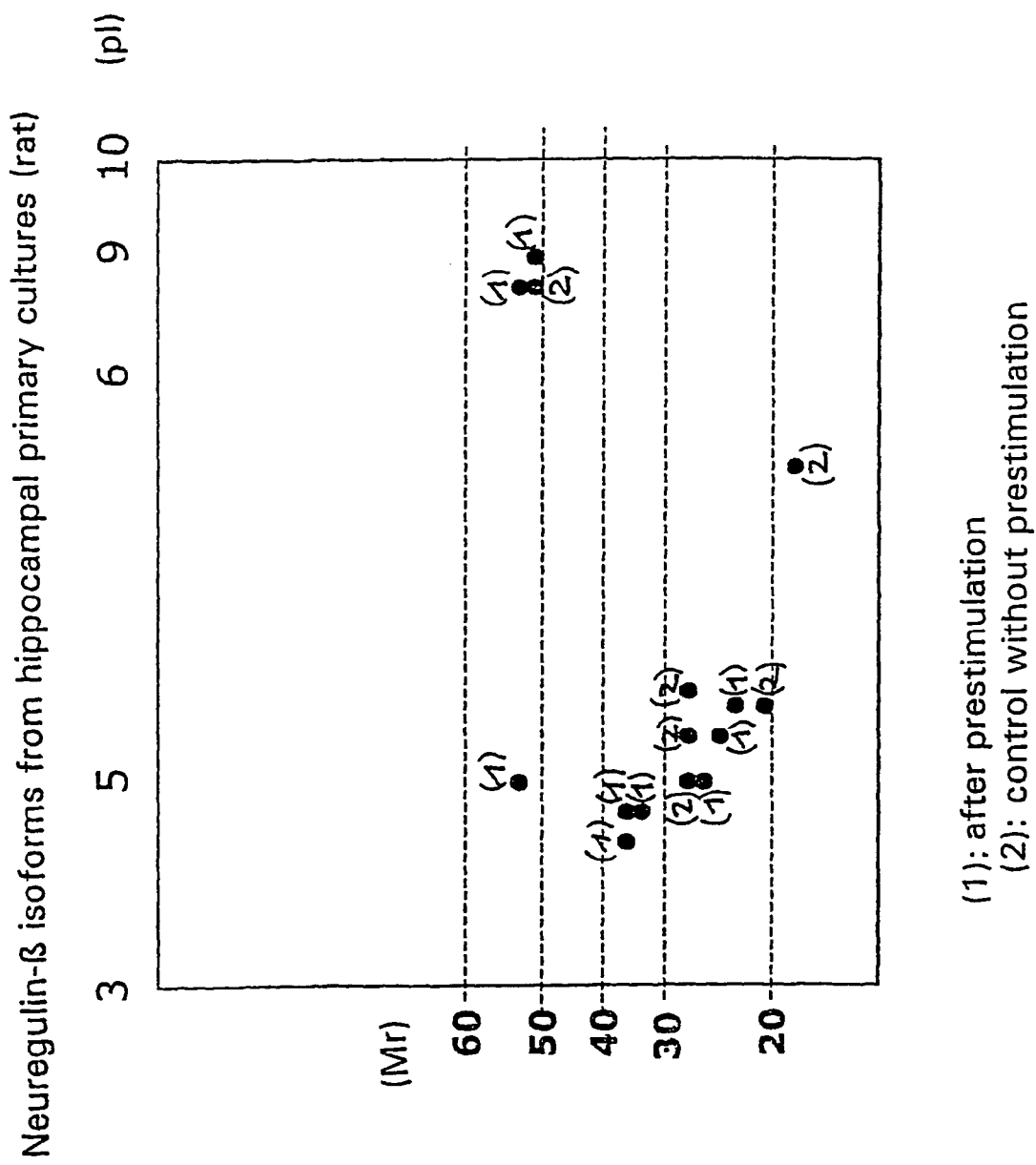
FIG. 2 shows neuregulin-β isoforms from hippocampal primary cultures (rat).
(1): after prestimulation.
(2): control without prestimulation.

The results of the proteomics analysis from hippocampal tissue sections or hippocampal primary cell cultures are shown in FIGS. 1 and 2.

The neuregulin-β isoforms or isoform pattern depicted in the figures are targets for diagnosis and therapy of neuronal disorders.

3. Example: Learning in the Radial 8-Arm Maze

Three groups of test animals, each consisting of three rats, are tested. Physiological saline solution is injected into the rats of group I and their learning behaviour in the 8-arm maze is tested. MK-801, a specific NMDA receptor antagonist, is injected into the rats of group II and their learning behaviour in the 8-arm maze is tested, too. Physiological saline solution is also injected into the rats of group III, but they are not released in the maze, but serve as control.

Figure 3:
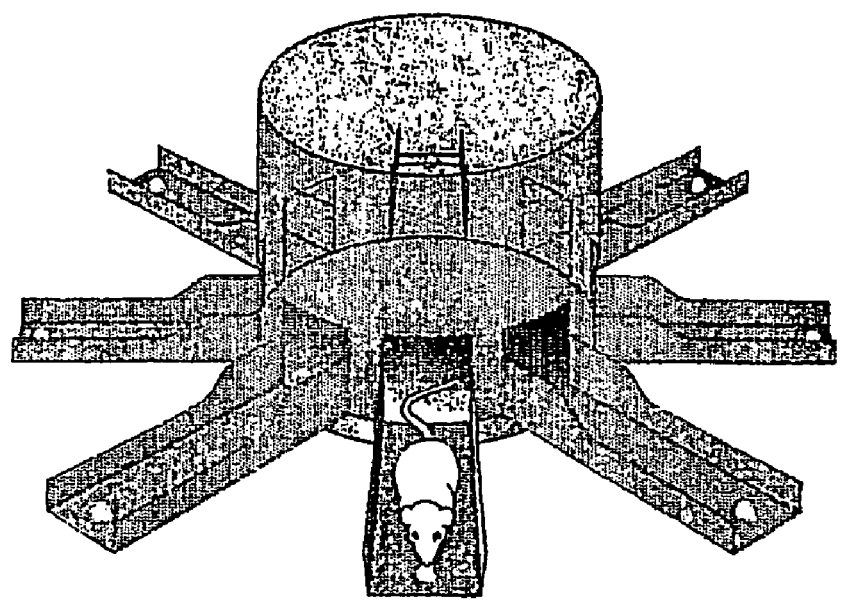
FIG. 3 shows the 8-arm maze used for animal testing.

Test Protocol 60 minutes after injection the animal is released in the maze (cf. FIG. 3). Every animal has to run through the maze 10 times, wherein every run is stopped, as soon as the animal has discovered the food at the end of each arm of the maze. If the animal has not found all the food after 4 minutes, the maze run is stopped.

The arms of the maze with the food source are disposed in the same way during every run of the animal. On the other hand, different animals have different "food arms" disposition in the maze. However, the position of the starting arms, i.e. the arm of the maze from which the animals starts their runs, vary for every run.

Every animal is released into the maze for 5 times 10 runs in a rhythm of 1 week. Each run of an animal in the maze is controlled and analyzed by a computer, wherein the maze run is followed on a monitor. The entering into or the leaving of a maze arm by the animal is detected with the help of a photo-electric barrier, wherein the number of entries of an animal in a maze arm are registered.

Subsequently, the data from this test are evaluated statistically and result in a number of measured values, which can be correlated directly with the learning behaviour of the rats. The values evaluated during this test are as follows:

PL positive runs, i.e. the running time is less than 1 minute
AB=number of entries into one arm
GF=total of failures, i.e. the sum of RM+WM
RM=reference memory failure
WM=working memory failure These parameters are correlated with the concentration of the memory-relevant neuregulin-β isoforms at about pI 5, which is determined densitometrically from Western blots by measurement of the SV (spot volume) parameter.

Figure 4:
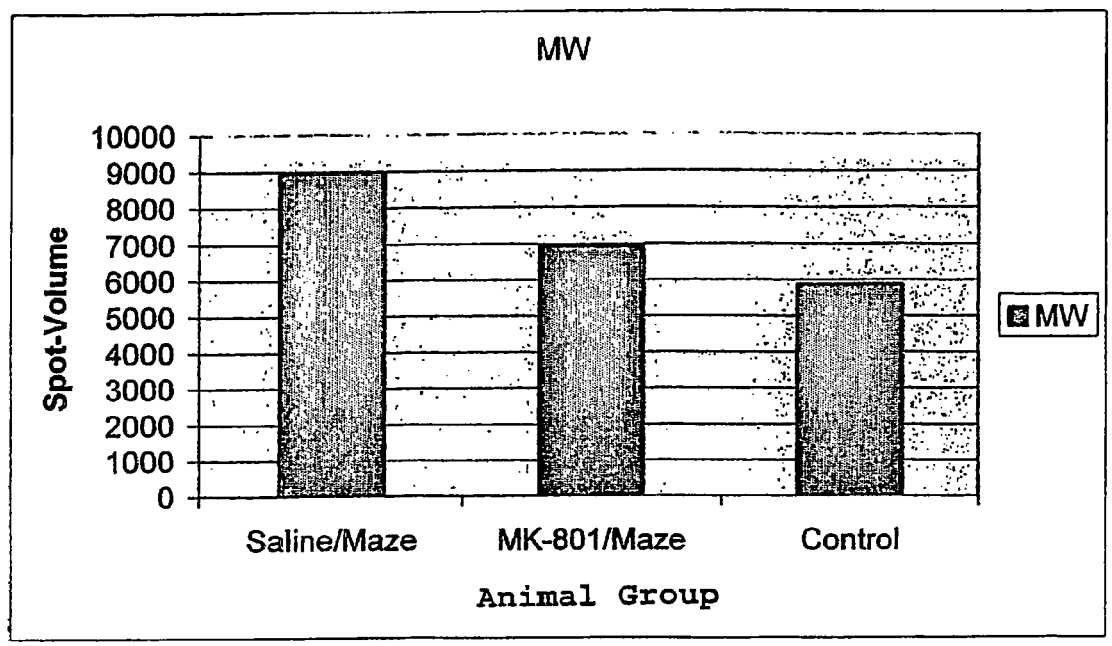
FIG. 4 shows the correlation of average concentration of memory-relevant neuregulin-β isoforms at about pI 5 of the three groups of test animals in the behaviour experiment.

The global result of the neuregulin-β isoform concentration average of the three groups of tested animals results in the statistically significant relations as illustrated in FIG. 4:

The group of the three rats, which have learned, i.e. those rats which have passed the maze training after the injection of saline, exhibit an average SV of 8994. The group of the three rats, which have passed the maze training under the influence of MK-801, exhibits an average SV of 6951, whereas the control group without maze training exhibits an average SV of 5886.

Figure 5:
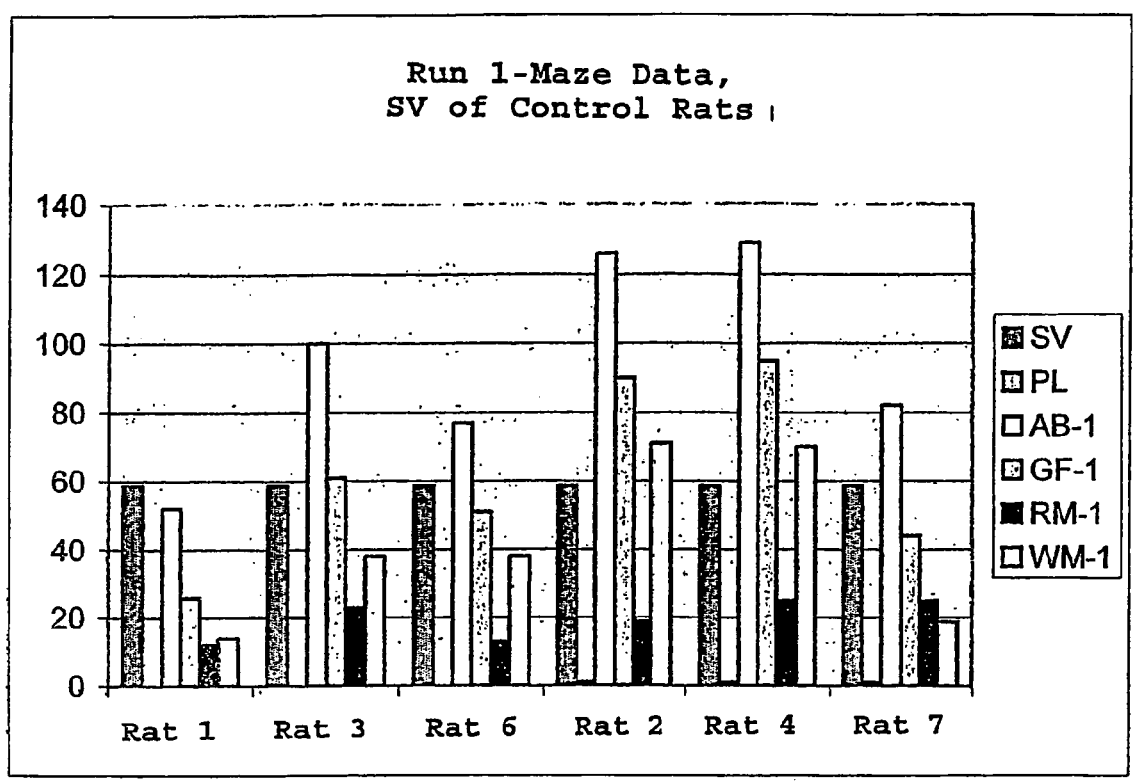
FIGS. 5 and 6 show the statistical evaluation and graphic correlation of the concentration of the particularly memory-relevant neuregulin-β isoforms at about pI 5 and the decisive measured values of the behaviour experiment.
Figure 6:
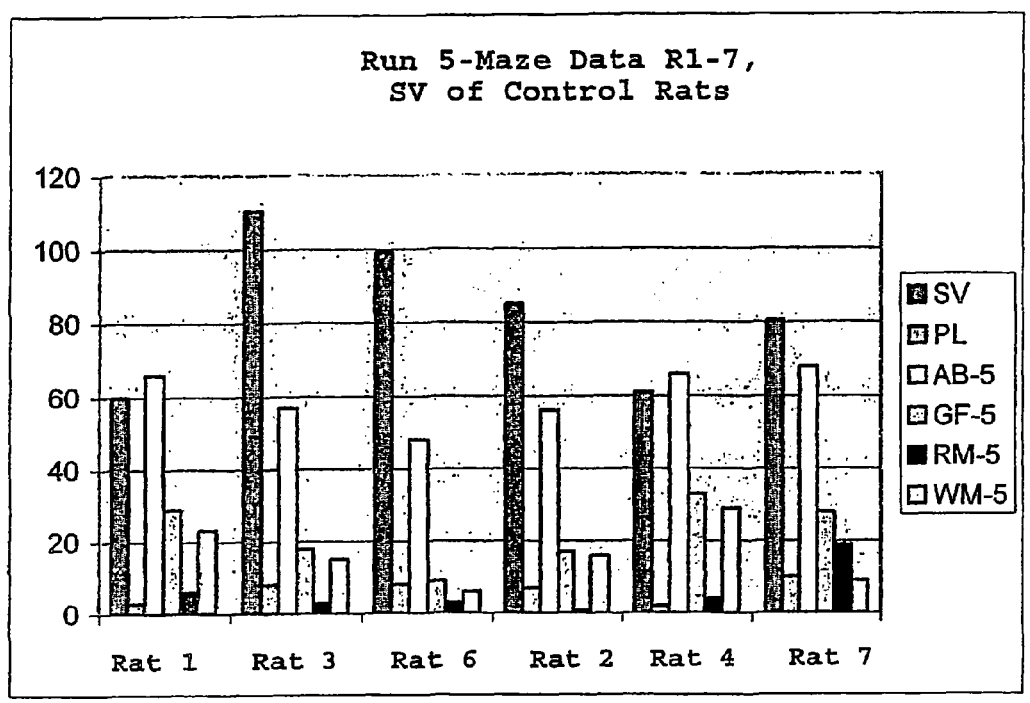
Figure 7:
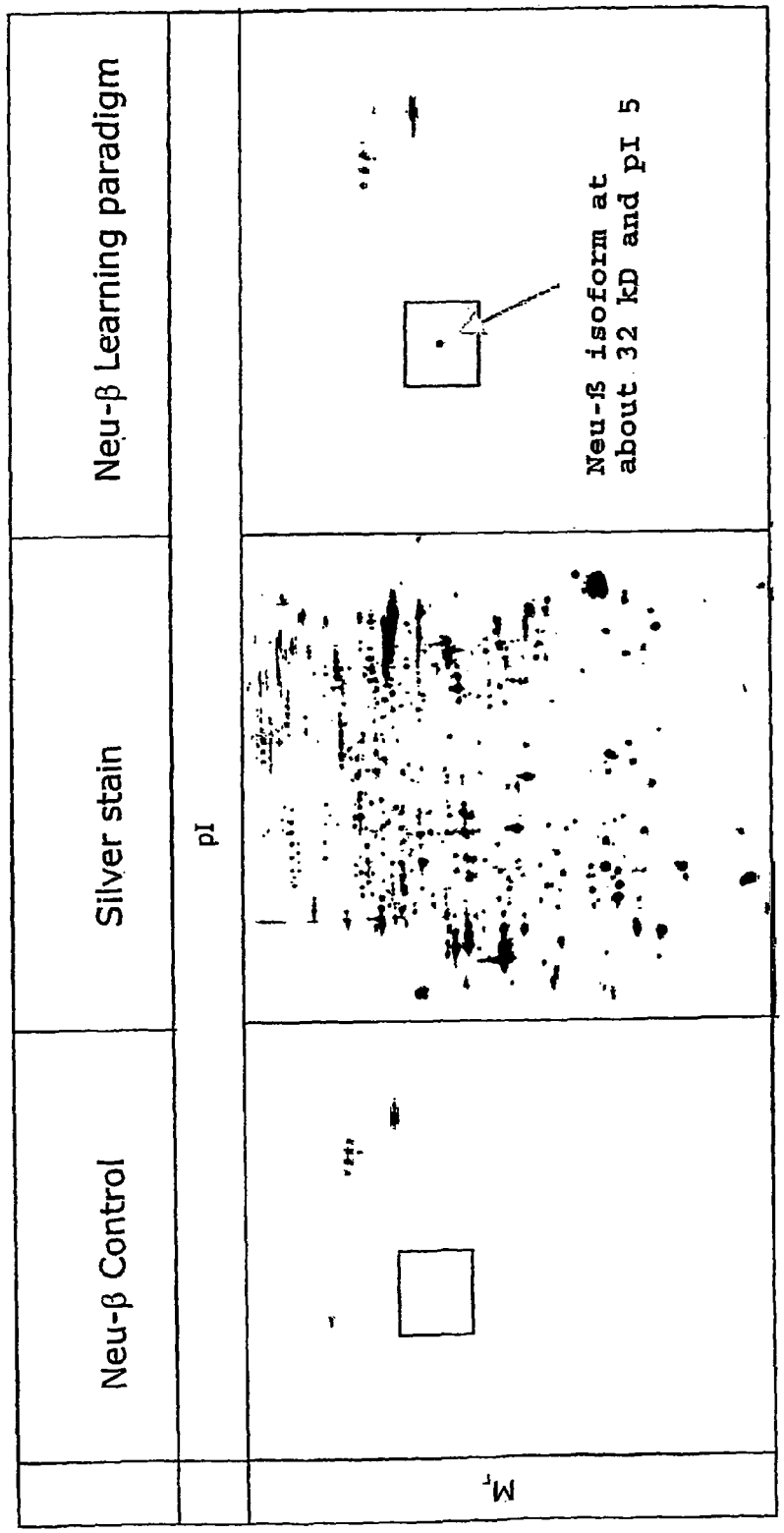
FIG. 7 shows 2D-gel and Western blot images for the isoform analysis of neuregulin-β in the behaviour model (rat).

In FIGS. 5 and 6 the test results are depicted. The diagrams show, for each rat of the two groups (rat 1, 3 and 6 belong to group I and rats 2, 4 and 7 belong to group II), the statistical evaluation and the graphical correlation of the concentration of the particular memory-relevant neuregulin-β isoforms at about pI 5 with the decisive measured values of the behaviour experiment. In FIG. 5 the relations of neuregulin-β SV are illustrated before learning, i.e. they correspond to the measurement of the first maze run, whereas in FIG. 6 the relations of neuregulin-β SV are shown after learning, i.e. they correspond to the measurements of the fifth maze run. It can be gathered from these diagrams that the rats, which have learned something between the first and the last maze run increase their positive runs and the total of failures and particularly the failures in the "working memory" (WM) are drastically decreased. These changes correlate almost perfectly with the increase of the spot volume of the neuregulin-β isoform at about pI 5 (SV). However, it was found that the expected learning blockade caused by MK-801 may indeed vary in individual rats. Rats 2 and 7, into which the specific NMDA-receptor antagonist was injected, still show a quite good learning behaviour despite MK-801. Consequently, these two rats significantly increase the average SV of their group. On the other hand, rat 1 of group I seems to be a rather dumb rat. In spite of missing pharmacological inhibition, it has improved only slowly. Also here the learning behaviour correlates with SV, it considerably decreases the average of the learning group.

The invention claimed is:

1. A method of screening for agents that increase or decrease the expression level of a neuregulin-β isoform, comprising the steps of:
   a) administering said biological agent to a test mammal,
   b) subjecting said test mammal and a control mammal to a maze test, wherein said control mammal has not been administered said biological agent,
   c) determining an expression pattern of a neuregulin-β isoform which has an isoelectric point (pI) in the range from pH 4.3 to 5.0, wherein said neuregulin-β isoform has an apparent molecular mass of about 32 kd as determined using 2 dimensional electrophoresis and mass spectrometry, of said test mammal and said control mammal,
   d) comparing said expression pattern of said test mammal and said control mammal to determine if the two expression levels are the same, or if said biological agent increased or decreased the expression levels of said neuregulin-β isoform, wherein an increase or decrease in the expression level of said neuregulin-β isoform in said test mammal's hippocampal tissue indicates that said biological agent increased or decreased the expression level of said neuregulin-β isoform,
   wherein said test mammal is a rat.

2. The method of claim 1, wherein the step of determining an expression pattern comprises 2-dimensional electrophoresis, wherein a first dimension is isoelectric focusing.

* * * * *